(12) United States Patent
Li

(10) Patent No.: US 8,188,438 B2
(45) Date of Patent: May 29, 2012

(54) ELECTROKINETIC MICROFLUIDIC FLOW CYTOMETER APPARATUSES WITH DIFFERENTIAL RESISTIVE PARTICLE COUNTING AND OPTICAL SORTING

(75) Inventor: Dongqing Li, Waterloo (CA)

(73) Assignee: Diagnostics Chips, LLC, Burlington, NC (US)

(*) Notice: Subject to any disclaimer, the term of this patent is extended or adjusted under 35 U.S.C. 154(b) by 163 days.

(21) Appl. No.: 12/719,262

(22) Filed: Mar. 8, 2010

(65) Prior Publication Data

US 2011/0089328 A1   Apr. 21, 2011

Related U.S. Application Data

(60) Provisional application No. 61/253,279, filed on Oct. 20, 2009.

(51) Int. Cl.
*G01T 1/20* (2006.01)
(52) U.S. Cl. .................................................. 250/364
(58) Field of Classification Search .......... 250/364; 435/39, 286.5, 34, 288.7; 264/219, 483
See application file for complete search history.

(56) References Cited

U.S. PATENT DOCUMENTS

| | | | |
|---|---|---|---|
| 6,337,740 B1 * | 1/2002 | Parce | 356/344 |
| 6,613,512 B1 * | 9/2003 | Kopf-Sill et al. | 435/6.19 |
| 7,306,924 B2 * | 12/2007 | Gomez et al. | 435/7.2 |
| 7,569,382 B2 | 8/2009 | Li | |
| 2005/0148064 A1 * | 7/2005 | Yamakawa et al. | 435/287.2 |
| 2005/0191620 A1 | 9/2005 | McDevitt et al. | |
| 2008/0003142 A1 * | 1/2008 | Link et al. | 422/82.08 |
| 2008/0070311 A1 | 3/2008 | Li | |
| 2008/0213821 A1 | 9/2008 | Liu et al. | |
| 2010/0136544 A1 * | 6/2010 | Agresti et al. | 435/6 |

OTHER PUBLICATIONS

Xu et al., "Fabrication and testing investigation of low-voltage integrated electrophoresis chip based on silicon-on-insulator-MEMS," 2007, Journal of Micro/Nanolithography, MEMS MOEMS, vol. 6, No. 3 pp. 033009-1-03009-7.*

Zahow et al., "Guided microfluidics by electromagnetic capillary focusing," 2002, Applied Physics Letters, vol. 80, No. 8, pp. 1483-1486.*

Fu et al., "Multiple volume injection technique for high-resolution DNA sample detection utilizing planar microfluidic chip," 2004, Proceedings of the 26th Annaul International Conference of the IEEE EMBS, San Francisco, CA, USA, pp. 50175020.*

(Continued)

*Primary Examiner* — Kiho Kim
(74) *Attorney, Agent, or Firm* — Myers Bigel Sibley & Sajovec, P.A.

(57) ABSTRACT

An electrokinetic microfluidic flow cytometer apparatus can include a substrate, a pair of signal and noise detection channels, and a particle detection circuit. The substrate includes an input port, an output port, and a microchannel that fluidly connects the input port and the output port to allow fluid to flow therebetween. The signal and noise detection channels are defined in the substrate and are fluidly connected to the microchannel from locations that are adjacent to each other. The signal and noise detection channels extend in opposite directions away from the microchannel to receive ambient electrical noise. The particle detection circuit generates a particle detection signal in response to a differential voltage across the signal and noise detection channels, which tracks changes in resistivity across an adjacent portion of the microchannel while at least substantially canceling a common component of the ambient electrical noise.

34 Claims, 8 Drawing Sheets

OTHER PUBLICATIONS

Zhang et al., "Methods for counting particles in microfluidic applications." Microfluid Nanofluid (2009) 7:739-749, Aug. 20, 2009, pp. 739-749.

Notification of Transmittal of the International Search Report and the Written Opinion of the International Search Authority, or the Declaration; International Search Report and Written Opinion; Corresponding to International Application No. PCT/US2010/050620; Date of Mailing: Nov. 22, 2010; 12 pages.

Chabinyc, Michael L. et al. "An Integrated Fluorescence Detection System in Poly(dimethylsiloxane) for Microfluidic Applications" *Analytical Chemistry* 73:4491-4498 (2001).

Cui, L. et al. "Optical particle detection integrated in a dielectrophoretic lab-on-a chip" *Journal of Micromechanics and Microengineering* 12:7-12 (2002).

Fu, Lung-Ming et al. "Electrokinetically driven micro flow cytometers with integrated fiber optics for on-line cell/particle detection" *Analytica Chimica Acta* 507:163-169 (2004).

Lee, Gwo-Bin et al. "Micro flow cytometers with buried SU-8/SOG optical waveguides" *Sensors and Actuators A* 103:165-170 (2003).

Mogensen, Klaus B. et al. "Integration of polymer waveguides for optical detection in microfabricated chemical analysis systems" *Applied Optics* 42(19):4072-4079, Jul. 1, 2003.

Rodriguez, William R. et al. "A Microchip CD4 Counting Method for HIV Monitoring in Resource-Poor Settings" *PLoS Medicine* 2(7):0663-0672 (2005).

Tung, Yi-Chung et al. "PDMS-based opto-fluidic micro flow cytometer with two-color, multi-angle fluorescence detection capability using PIN photodiodes" *Sensors and Actuators B* 98:356-367 (2004).

Xiang, Qing et al. "Multi-Functional Particle Detection with Embedded Optical Fibers in a Poly(dimethylsiloxane) Chip" *Instrumentation Science and Technology* 33:597-607 (2005).

\* cited by examiner

FIGURE 9
Individual CD4 Blood Cells Detected in Sample Using Optical Particle Characteristic Detection Apparatus
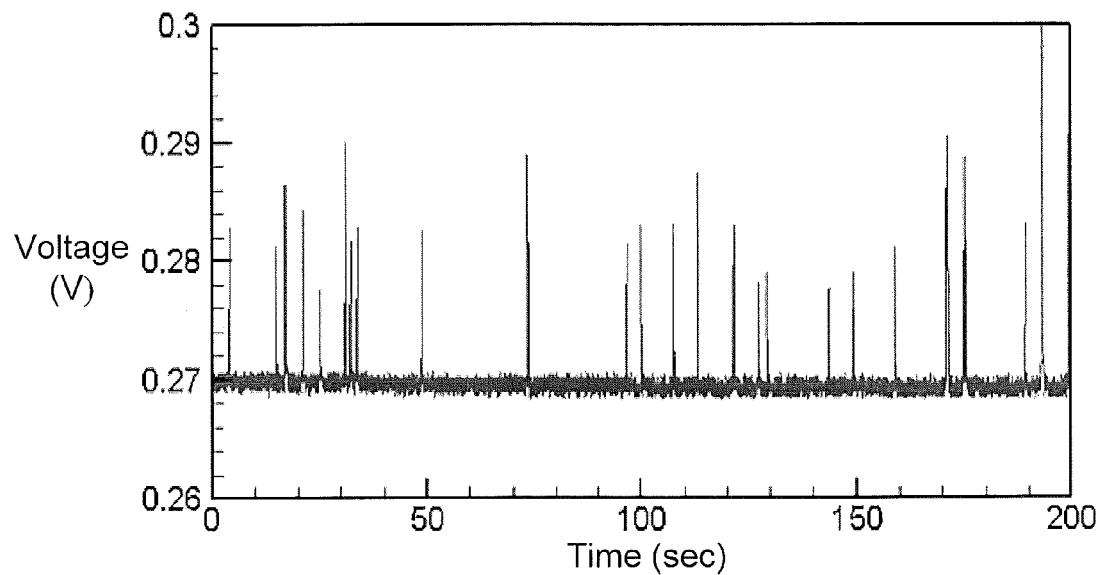
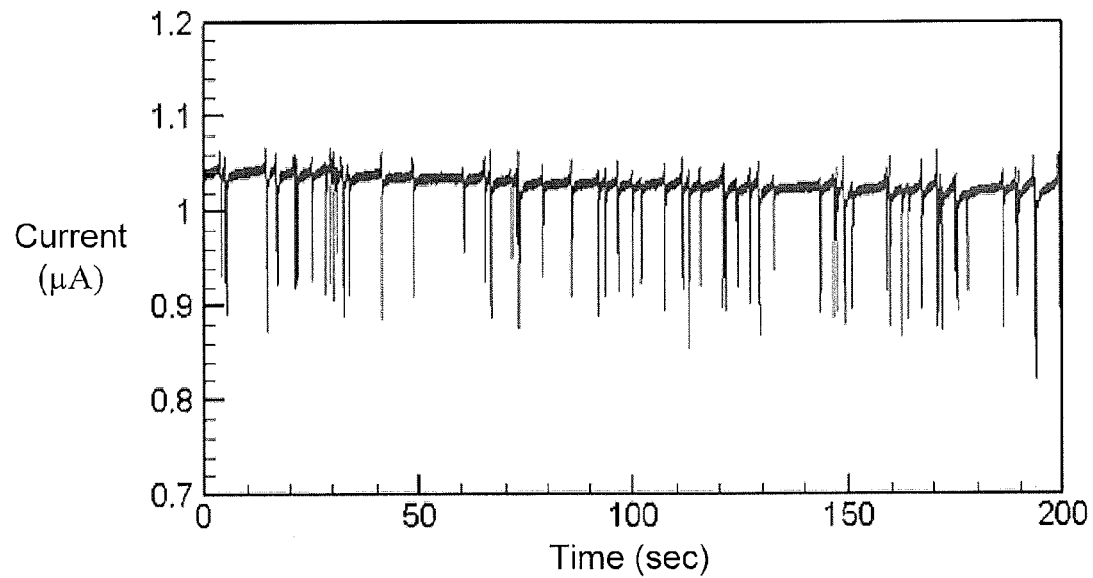
Detected Sequence of Blood Particles, Including Some CD4 Cells, Moving One By One Through Particle Counting Sensor
FIGURE 10

ELECTROKINETIC MICROFLUIDIC FLOW CYTOMETER APPARATUSES WITH DIFFERENTIAL RESISTIVE PARTICLE COUNTING AND OPTICAL SORTING

CROSS-REFERENCE TO RELATED APPLICATIONS

This U.S. non-provisional patent application claims priority to U.S. Patent Application No. 61/253,279, filed on Oct. 20, 2009, the entire contents of which are hereby incorporated by reference.

FIELD OF THE INVENTION

The invention generally relates to the field of microfluidics, and more particularly to microfluidic flow cytometers and applications of same.

BACKGROUND

Flow cytometry provides a method of detecting and analyzing cells or particles contained in a sample, for example, blood cells in blood such as red blood cells (erythrocytes), white blood cells (leukocytes) and blood platelets (thrombocytes), or material components in urine such as bacteria, blood cells, epithelial cells or casts. These cells or material components may increase or decrease in number responsive to onset or progression of a disease. Accordingly, a disease can be diagnosed by detecting the status of each cell or material component on the basis of information about granules or particles in the sample.

Flow cytometer measures the number of cells and detects the number of a specific type of cells by optical processes such, as light scattering and fluorescence measurement, as the cells travel in suspension one by one passing a sensing point. Some flow cytometers from well-known vendors such as Beckman-Coulter or Becton Dickenson are expensive, with the cost ranging from $75,000-$125,000 which limits their availability to large reference laboratories. In addition to the initial cost of the instrument, service contracts for these instruments are typically 10% of the cost of the instrument on an annual basis. In addition, the sample volumes are usually large, such as in the 100 microliter range, and the necessary reagent volumes are correspondingly expensive.

For example, in the field of HIV treatments, an important parameter for determining disease staging is the number of CD4+ T cells (unit of cells/mm$^3$) in peripheral blood. However, the laboratory evaluation of CD4+ T cell numbers can be cumbersome and expensive. Typically, the total lymphocyte count is determined by a routine CBC (complete blood count) assay, the percentage of CD4+ T lymphocytes as a function of total lymphocytes is determined by flow cytometry, and these values are multiplied to determine an absolute CD4+ T cell number. This analysis is expensive, time consuming and generally not locally available for less wealthy regions of the United States and the world.

Many clinical applications require frequent blood tests to monitor patients' status and the therapy effectiveness. It is highly desirable to use only small volume blood samples from patients for each test. Furthermore, it is highly desirable to have affordable and portable flow cytometry instruments for field applications, point-of-care applications and applications in resource-limited locations. Recently, efforts have been made to apply microfluidic technologies to flow cytometric analysis of cells to attempt to manufacture small sized portable flow cytometers.

SUMMARY OF EMBODIMENTS OF THE INVENTION

Some embodiments of the present invention are directed to an electrokinetic microfluidic flow cytometer apparatus. The apparatus includes a substrate, a pair of signal and noise detection channels, and a particle detection circuit. The substrate has defined therein an input port, an output port, and a microchannel that fluidly connects the input port and the output port to allow fluid to flow therebetween. The signal and noise detection channels are defined in the substrate and are fluidly connected to the microchannel from locations that are adjacent to each other. The signal and noise detection channels extend in opposite directions away from the microchannel to receive ambient electrical noise. The particle detection circuit is electrically connected to the signal and noise detection channels and generates a particle detection signal in response to a differential voltage across the signal and noise detection channels that tracks changes in resistivity across an adjacent portion of the microchannel as particles within the fluid move responsive to an electric field along that portion of the microchannel. The particle detection circuit at least substantially cancels a common component of the ambient electrical noise received by the signal and noise detection channels while it generates the particle detection signal.

The apparatus can further include a particle counting circuit that counts a number of particles that move through the sensing gate in response to pulses in the particle detection signal. Two electrodes can be positioned within different ones of the input port and an output port. A control circuit can control application of an electric voltage across the electrodes to create an electric field along the microchannel and an electrokinetic force which transports fluid from the input port to the output port. A sensing gate can be included that reduces the cross sectional area of the microchannel through which fluid carrying particles can flow to increase the resistivity changes that occur as each particle moves through the sensing gate. The signal and noise detection channels can be fluidly connected to the microchannel at locations that are adjacent to the same sides or opposite sides of the sensing gate to sense ambient electrical noise incident to the sensing gate. The signal and noise detection channels can be structurally identical to each other so that they are configured to receive about equal amounts of ambient electrical noise. The particle detection circuit can generate the particle detection signal responsive to resistivity changes that occur across the sensing gate as particles flow through the sensing gate in the presence of the electric field along the microchannel. The particle detection circuit may include a differential amplifier having a pair of input terminals that are electrically connected to electrodes positioned within a fluid carrying space of different ones of the signal and noise detection channels.

Some other embodiments of the present invention are directed to an electrokinetic microfluidic flow cytometer apparatus that includes a substrate, at least one optical fiber, a primary photodetector, a reference photodetector, and a comparator circuit. The substrate has defined therein an input port, a plurality of particle sorting output ports, and a microchannel that fluidly connects the input port and the plurality of particle sorting output ports to allow fluid to flow therebetween responsive to an electric field along the microchannel. The optical fiber is positioned to guide at least one wavelength of coherent laser light from at least one laser light source to illuminate an optical detection region of the microchannel and to collect light that is emitted from at least one particle present in fluid within the optical detection region. The primary photodetector is connected to the at least one optical fiber to receive at least first wavelength light therefrom and is configured to generate a first output signal responsive thereto. The first output signal contains a noise component, which may arise due to, for example, temperature effects and/or other properties of the analog circuitry of the photodetector sensors and/or the associated sampling circuitry and/or analog-digital circuitry. The reference photodetector generates a reference noise signal that is not responsive to any light collected from the optical detection region of the microchannel and is therefore characteristic of the noise component in the first output signal. The first comparator circuit generates a first characterization signal responsive to a difference between the first output signal and the reference noise signal so that the first characterization signal is at least substantially free of the noise component from the first output signal.

The reference photodetector can have substantially the same operational characteristics as the primary photodetector, such as by being manufactured using the same processes as the primary photodetector. The comparator circuit can include a differential amplifier having a pair of input terminals, one is connected to receive the first output signal from the primary photodetector and the other is connected to receive the reference noise signal from the reference photodetector. A differential amplifier generates a first particle characterization signal responsive to a voltage difference between the input terminals that indicates a detected optical characteristic of a particle within the optical detection region responsive to illumination by the at least one wavelength of coherent laser light. A control circuit can be configured to classify the particle as being a defined particle type in response to the first particle characterization signal. A particle sorting circuit can separately control voltages between a plurality of particle sorting output ports and at least the optical detection region of the microchannel in response to at least the first characterization signal to transport the at least one particle by electrokinetic flow of the fluid from the optical detection region to one of the output ports that is selected responsive to the at least the first characterization signal.

Other apparatuses, components, and associated operational methods according to embodiments of the invention will be or become apparent to one with skill in the art upon review of the following drawings and detailed description. It is intended that all such additional apparatuses, components, and associated operational methods be included within this description, be within the scope of the present invention, and be protected by the accompanying claims. Moreover, it is intended that all embodiments disclosed herein can be implemented separately or combined in any way and/or combination.

BRIEF DESCRIPTION OF THE DRAWINGS

The accompanying drawings, which are included to provide a further understanding of the invention and are incorporated in and constitute a part of this application, illustrate certain embodiment(s) of the invention. In the drawings:

FIG. 9 is a graph illustrating a particle characterization voltage signal that was output during operation of an exemplary particle optical characterization apparatus similar to that illustrated in FIGS. 1 and 7 (e.g., the signal output by one of the differential amplifiers in FIG. 7) and which identifies by pulsed changes when individual fluorescent dyed CD4 cells within a blood sample are optically sensed using a defined wavelength coherent laser light;

FIG. 10 is a graph illustrating a particle counting signal that was output during operation of the particle counting sensor of the exemplary apparatus of FIGS. 1 and 7 as a sequence of blood particles, including some CD4 cells, moves one by one through the particle sensing gate of the particle counting sensor;

DETAILED DESCRIPTION OF EMBODIMENTS OF THE INVENTION

Figure 1:
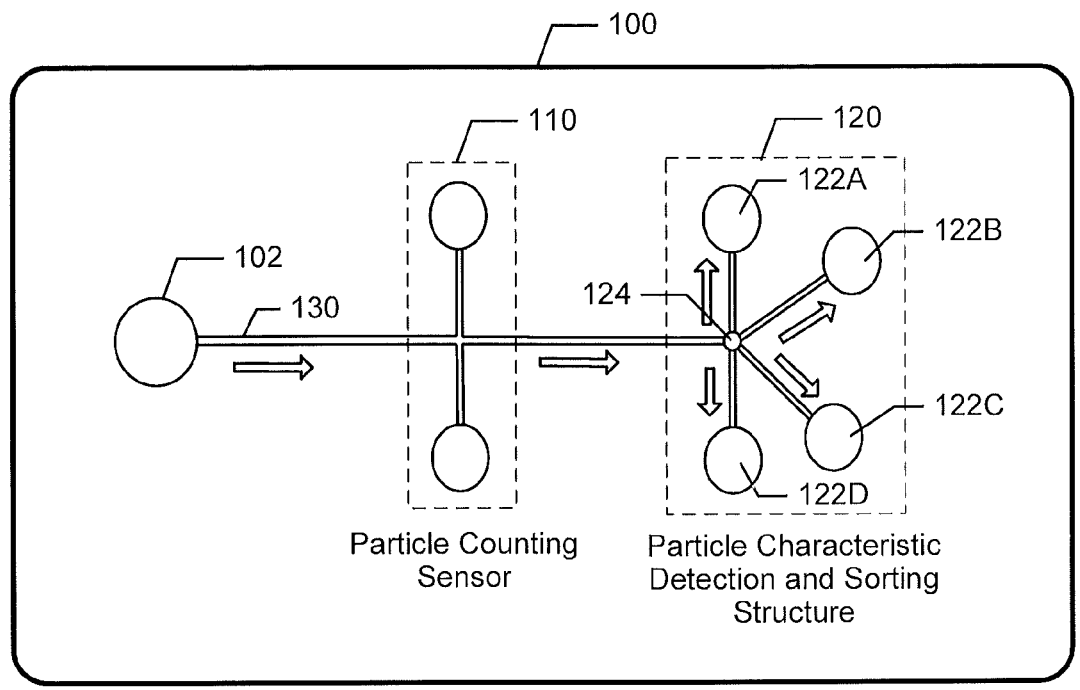
FIG. 1 is a plan view of an electrokinetic microfluidic flow cytometer chip having a particle counting sensor with signal and noise detection channels and a particle characterization and sorting structure that are configured according to some embodiments of the present invention.

The invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, when an element is referred to as being "coupled" to another element, it can be directly coupled to the other element or intervening elements may be present. In contrast, when an element is referred to as being "directly coupled" to another element, there are no intervening elements present. Like numbers refer to like elements throughout.

Spatially relative terms, such as "above", "below", "upper", "lower" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly. Well-known functions or constructions may not be described in detail for brevity and/or clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

Embodiments of the invention are described herein with reference to schematic illustrations of idealized embodiments of the invention. As such, variations from the shapes and relative sizes of the illustrations as a result, for example, of manufacturing techniques and/or tolerances, are to be expected. Thus, embodiments of the invention should not be construed as limited to the particular shapes and relative sizes of regions illustrated herein but are to include deviations in shapes and/or relative sizes that result, for example, from different operational constraints and/or from manufacturing constraints. Thus, the elements illustrated in the figures are schematic in nature and their shapes are not intended to illustrate the actual shape of a region of a device and are not intended to limit the scope of the invention. The relative sizes of various portions of the illustrate structures may be exaggerated for ease of illustration and explanation.

Various embodiments of the present invention are directed to an electrokinetic microfluidic flow cytometer apparatus which may be sufficiently miniaturized so as to be hand-held or otherwise transportable. Some of the apparatus structure is defined in a substrate, such as a chip/wafer, which can be operated to provide rapid highly accurate flow cytometry analysis from a small volume fluid sample. Various embodiments are described herein in the context of flow cytometers that are configured as a functional laboratory-on-a-chip, where the chip may be formed from various types of substrates. Moreover, some embodiments are described herein in the context of using flow cytometers to analyze cells within a blood sample, however the invention is not limited thereto and may be applied much more broadly for analyzing any type of particles within fluid.

Some embodiments provide a miniaturized flow cytometer that regulates fluid transport through microchannels defined in a chip. The chip includes a particle counting sensor and a particle characterization and sorting structure. The fluid is transported through the microchannels using electric fields that generate electrokinetic forces on the fluid. This electrokinetic microfluidic flow can avoid the need for an external pump, valves and piping system, and enable the flow cytometer to be sufficiently miniaturized so as to be easily transportable and even made handheld.

When a solid surface is in contact with an aqueous solution, electrostatic charge will be established along the surface. These surface charges in turn attract the counter ions in the liquid to a region close to the solid-liquid interface which forms an electrical double layer (EDL). In the electrical double layer region, there are excess counter ions (net charge). When an external electrical field is applied tangentially to the solid surface, the excess counter ions will move under the influence of the applied electrical field, pulling the liquid with them and resulting in electroosmotic flow. The liquid movement is carried through to the rest of the liquid in the microchannel by viscous effects. In contrast, pumping a liquid through a small microchannel requires applying a very large pressure difference depending on the flow rate, and such pumping may not be possible for microchannel fluid flow because of the limited size and mechanical strength of microfluidic devices. Electroosmotic flow however can generate desired fluid flow rates in very small microchannels without any externally applied pressure difference by controlling the applied electrical fields via electrodes are inserted in different wells at the ends of the microchannels. Electroosmotic flow can thereby be used to transport liquids through the microchannels without employing external mechanical pumps, tubing and valves. The fluid flow rate can be controlling by regulating strength of the applied electrical fields.

Electrophoresis is the motion of a charged particle relative to the surrounding liquid under an applied electrical field. In a microchannel, the net velocity of a charged particle is determined by the electroosmotic velocity of the liquid and the electrophoretic velocity of the particle. If the surface charge of the particle is not strong or the ionic concentration of the liquid (e.g., typical buffer solutions) is high, the particle will move with the liquid. Using electrical fields to manipulate and transport biological cells in microchannels is particularly suitable for various embodiments of the present invention to provide a functional laboratory-on-a-chip.

According to various embodiments, a handheld/transportable flow cytometer lab-on-a-chip device can include an electrokinetic microfluidic flow cytometer chip, a differential electric resistive pulse sensor that is configured to count particles (e.g., blood cells, etc.) within a fluid sample, a miniaturized laser-fiber particle optical characterization apparatus that is configured to detect particle optical characteristics and to count numbers of different defined types of particles (e.g., by detecting specific fluorescent dye labels on the particles), and an operation control circuit and display unit.

1. The Electrokinetic Microfluidic Flow Cytometer Chip.

FIG. 1 is a plan view of an electrokinetic microfluidic flow cytometer chip 100 that is configured in accordance with some embodiments of the invention. Referring to FIG. 1, the illustrated straight lines represent fluid conduit microchannels and the circles represent ports (liquid wells/reservoirs). The drawing of FIG. 1 is for exemplary illustration only, accordingly its illustrated elements are not shown to actual or relative scale.

The exemplary cytometer chip 100 can include three primary functional areas that are interconnected by at least one microchannel 130 which provides a conduit for fluid flow therethrough. One functional area can include an input port 102 (well/reservoir), illustrated on the left side of the chip 100, which is configured to hold a sample solution. The sample solution may be a buffer solution containing a blood sample that is to be analyzed using the cytometer chip 100. A second functional area can include a particle counting sensor 110 that is configured to count the number of cells in the sample solution using a differential electrical resistance pulse sensor. A third functional area can include a particle characterization and sorting structure 120 that is configured to optically distinguish among various defined types of particles that pass through an optical detection region 124 thereof and to sort those particles among a plurality of output ports 122A-D responsive to their identification.

The sample solution is moved via the microchannel 130 from the input port 102 through particle counting sensor 110 and then through the particle characterization and sorting structure 120 by applying an electric field along the microchannel 130 that creates an electrokinetic force on the sample solution. Further electric fields can be generated and selectively controlled between at least the optical detection region 124 and selected output ports 122A-D to sort the particles. As will be explained in further detail below with regard to FIG. 7, a miniaturized laser-fiber optical system is configured to detect and classify the optical characteristics of particles passing through the optical detection region 124. For example, blood cells may be labeled with certain fluorescent dyes that can be optically identified as the cells move through the optical detection region 124.

The cytometer chip 100 may be manufactured by binding a thin polydimethylsiloxane (PDMS) plate (or other polymer materials or glass) to a glass slide. The cytometer chip 100 may alternatively be manufactured from two polymer plates or two glass slides, although other materials may be used. As shown in FIG. 1, the cytometer chip 100 has a microchannel network structure (e.g., microchannel 130) and several liquid ports (e.g., input port 102 and output ports 122A-D). When a thin polydimethylsiloxane (PDMS) plate is used as the top layer and a glass slide is used as the bottom substrate, the microchannel structure and ports can be made on the PDMS plate through a soft lithography patterning process, which can include photolithography and etching. During flow cytometry tests, the microchannel structure and ports 102, 122A-D are filled with liquids (sample and buffer solutions). The ports 102, 122A-D serve as not only the reservoirs for holding the liquids, but are also electrically connected to control circuitry through electrodes placed therein to generate the electric fields necessary for the electrokinetic fluid motion and for sensing particles flowing through the particle counting sensor 110, as will be explained in further detailed below. Because the cytometer chip 100 can be made from polymer materials and glass, it may be manufactured relatively inexpensively and, thereby, can be designed for disposable single use applications.

2. The Differential Electric Resistive Pulse Sensor.

In conventional flow cytometers, cell counting may be performed using an apparatus that detects light scattered as particles moving through a light beam or using a Coulter counter apparatus. Light scattering techniques can require a series of large and expensive optical components, such as lasers, optic filters and photomultiplier tubes, which may be difficult, or impossible, to miniaturize into a handheld or other portable device. A Coulter counter apparatus operates on the principle that when an electrically non-conducting particle moves through a narrow section of a microchannel, it affects the electric current flowing through that narrow section and causes a corresponding local voltage change which can be detected and counted. The sensitivity of a Coulter counter apparatus depends on the volume ratio of the particle relative to the channel. For relatively small particles, such as blood cells, a sufficient sensor sensitivity or signal-to-noise ratio may only be obtainable through the use of bulky and sophisticated electronic instruments such as Lock-In Amplifiers. Consequently, Coulter counter apparatuses may also be difficult, or impossible, to miniaturize into a handheld or other portable device.

Figure 2:
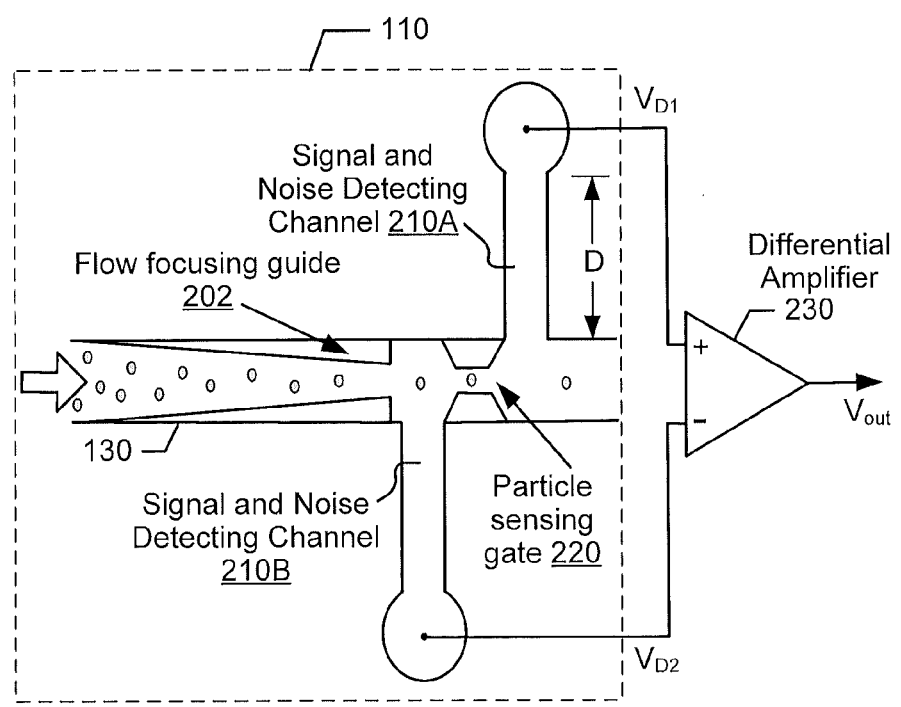
FIG. 2 is an enlarged view of the particle counting sensor of FIG. 1 and an associated differential amplifier circuit which are configured according to some embodiments of the present invention.

In some embodiments of the present invention, a microfluidic differential electric resistive pulse sensor is used to count particles that flow through the microchannel 130. FIG. 2 is an enlarged view of the particle counting sensor 110 of FIG. 1, which is configured as a microfluidic differential electric resistive pulse sensor, and an associated differential amplifier circuit 230 that outputs a particle detection signal Vout.

Referring to FIG. 2, the particle counting sensor 110 includes a pair of signal and noise detection channels 210A-B that are defined in a surface of the cytometer chip 100. The signal and noise detection channels 210A-B are fluidly connected to the microchannel 130 and extend in opposite directions away from the microchannel to receive ambient electrical noise that is incident to the chip 100. A particle sensing gate 220 reduces a fluid flow cross sectional area of the microchannel 130 through which fluid carrying particles can flow. The signal and noise detection channels 210A-B are fluidly connected to the microchannel 130 from locations that are adjacent to and on opposite sides of the particle sensing gate 220.

The differential amplifier 230 is electrically connected to the signal and noise detection channels 210A-B and generates the particle detection signal Vout in response to a differential voltage across the signal and noise detection channels 210A-B with the particle sensing gate 220 therebetween, which tracks changes in resistivity across particle sensing gate 220 as individual particles move therethrough. The differential amplifier 230 generates the particle detection signal Vout responsive to resistivity changes that occur across the sensing gate 220 as particles flow through the sensing gate 220 under an electric field applied along the microchannel 130. Accordingly, the electric field that is used to provide electrokinetic transport of the fluid and particles through the microchannel 130 may also be used to sense resistivity changes across the sensing gate 220 as particles flow therethrough. A particle counting circuit can be included, either on the cytometer chip 100 or separate therefrom, that is configured to count particles flowing through the particle counting sensor 110 responsive to pulses occurring in the particle detection signal Vout.

In one exemplary embodiment, the differential amplifier 230 can have two differential input terminals, one of which is connected to an electrode located in a fluid carrying portion of the detecting channel 210A to sense a voltage $V_{D1}$ therein and the other is connected to another electrode located in a fluid carrying portion of the other detecting channel 210B to sense a voltage $V_{D2}$ therein. The differential amplifier 230 can generate the particle detection signal Vout responsive to a differential voltage between the input voltages $V_{D1}$ and $V_{D2}$.

The ambient electrical noise that is received by each of the signal and noise detection channels 210A-B can have similar characteristics because they are closely located, similarly/identically configured, and are connected to the same microchannel 130. The ambient electrical noise may arise from external sources, such as from adjacent electrical power systems which radiate 60 Hz or other frequency noise and/or from computers, cell phones, and other electronic devices that radiate in a frequency range from hundreds of Hz and GHz. The signal and noise detection channels 210A-B may be structurally identical so that they receive equal amounts of ambient electrical noise. Because the differential amplifier 230 responds to a differential voltage across the signal and noise detection channels 210A-B, it can at least substantially cancel a common component of the ambient electrical noise received by the signal and noise detection channels 210A-B as the differential amplifier 230 generates the particle detection signal Vout.

When a particle passes through the sensing gate 220, a differential voltage is generated across the signal and noise detection channels 210A-B which is sensed and amplified by the differential amplifier 230. Although the differential voltage appearing across the input terminals of the differential amplifier 230 may have a relatively small amplitude, the amplitude of the differential voltage can be substantially enlarged by the gain of the differential amplifier 230. Thus, the present microfluidic differential electric resistive pulse type particle counting sensor 110 may provide a significant improvement in the signal-to-noise ratio in the detection of particles flowing through the sensing gate 200. For example, during testing of an exemplary counting sensor 110, accurate sensing was obtained for particles of 520 nanometers in diameter with a sensing gate having a volume of $50 \times 16 \times 20$ µm$^3$, which corresponds to a very low volume ratio of 0.0004% between the particle and the sensing gate. This volume ratio may be about ten times lower than what has been observed as the lowest volume ratio reported in literature, including what has been published as achievable for commercial Coulter counters. Accordingly, particle counting sensors that are configured in accordance with various embodiments of the present invention may provide high sensitivity and a small sensor size because of, for example, the use of a small sensing gate, two identical signal and noise detection channels, and a low electronic complexity differential amplifier.

Figure 3:
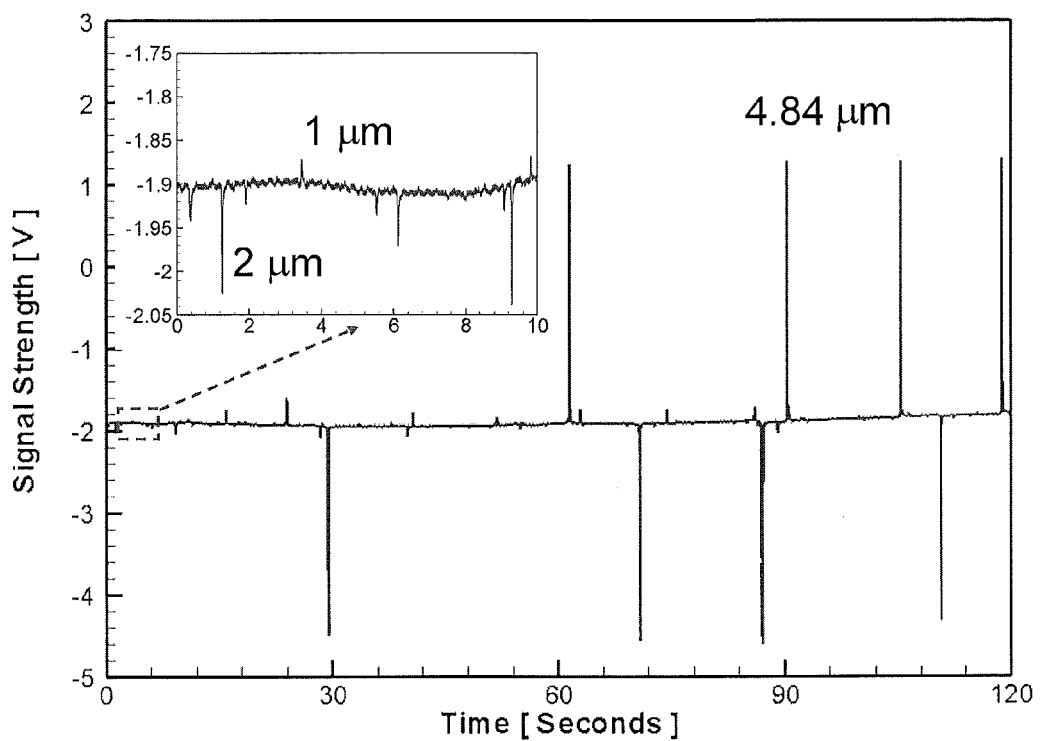
FIG. 3 is a graph illustrating a particle detection signal that was output during operation of an exemplary electrokinetic microfluidic flow cytometer chip similar to that illustrated in FIGS. 1 and 2 (e.g., the signal output by the differential amplifier of FIG. 2) as a sequential of particles moves one by one through the particle sensing gate.
Figure 4:
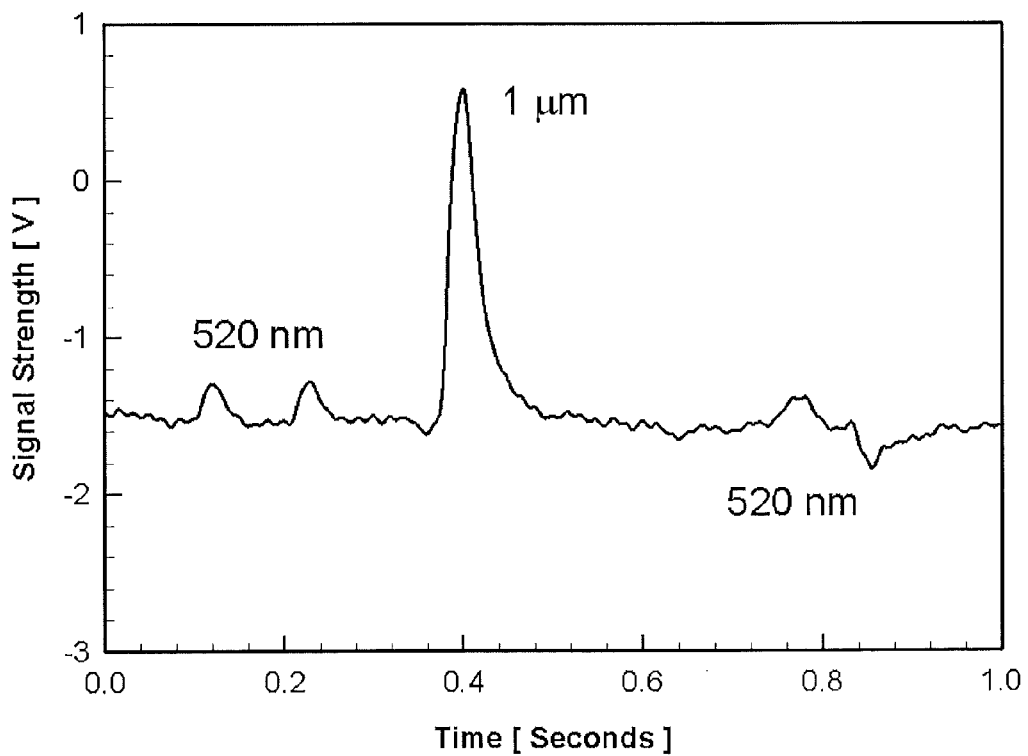
FIG. 4 is an enlarged view of the graph of FIG. 3 illustrating that a particle with about a 1 μm diameter can be detected as a pulse in the particle detection signal of FIG. 3.

FIGS. 3 and 4 illustrate graphs of exemplary results that were obtained during operational testing of a microfluidic differential electric resistive pulse type particle counting sensor which was similar to that shown in FIGS. 1 and 2. FIG. 3 illustrates the particle detection signal that was output by the differential amplifier as a sequence of particles suspended in 7.5 mM of a sodium borate buffer solution moved one by one through the particle sensing gate. Referring to FIG. 3 it is observed that 4.84 µm diameter particles (e.g., CD4 blood cells), 2 µm diameter particles, and 1 µm diameter particles, flowing through the particle sensing gate caused the differential amplifier to output a relatively large voltage pulse. A particle counting circuit can thereby accurately count the number of particles moving through the particle sensing gate in response to individual pulses of the particle detection signal.

FIG. 4 is an enlarged view of the graph of FIG. 3, with a different scale along the axis, illustrating that particles having a 520 nm diameter flowing through the particle sensing gate also caused the differential amplifier to output voltage pulses that are detectable above noise in the particle detection signal after cancellation of common components of the ambient electrical noise received by the signal and noise detecting channels 210A-B. The particle counting circuit that was tested may therefore be capable of accurately counting particles at least as small as 0.5 µm diameter gate. Through further balancing of the noise sensing characteristics of the signal and noise detection channels 210A-B, further improvements in the particle detection sensitivity may be obtained so that the particle counting circuit can accurately detect still smaller particles flowing through the particle sensing gate one at a time.

Referring again to FIG. 2, a flow focusing guide 202 can reside upstream of the detecting channels 210A-B and the sensing gate 220 and can function to cause the particles in the fluid to pass through the sensing gate 220 one at a time in a single line. The flow focusing guide 202 can be configured to have a cross sectional fluid flow area along the flow direction of the microchannel 202 that restricts particles flowing therethrough to exiting one at a time in a single line.

The sensing gate 220 can have a narrow fluid flow cross-sectional gap size that may range from sub-microns to tens of microns, depending upon the size of the to-be-detected particles. As shown in FIG. 2, the sensing gate can include a pair of members that extend toward each other from opposite facing sidewalls of a portion of the microchannel 130 to reduce the cross sectional area of the microchannel 130 through which the fluid flows, which increases the sensitivity of the particle counting sensor 110 to resistivity changes that occur between the members as individual particles flow between the members within the microchannel 130. The sensing gate 220 may be configured to reduce the cross-sectional width of the microchannel 130 through which fluid can flow to less than about ten times a width of individual particles that are to be sensed. For some flow cytometry applications, the sensing gate 220 may have a fluid flow cross-sectional gap size of between about 1 µm to about 50 µm to exhibit a resistivity change as particles flow therethrough that is sufficiently sensitive for accurate detection by the differential amplifier 230. The sensing gate 220 may have a length of between about 5 µm to about 100 µm along which it reduces the cross-sectional width of the microchannel 130.

To increase sensitivity of the signal and noise detecting channels 210A-B, they may each have a cross-sectional area that is less than a cross-sectional area of the microchannel 130 adjacent to where the signal and noise detection channels 220A-B fluidly connect to the microchannel 130. For example, the width of each signal and noise detection channel 220A-B may be less than half a width of the microchannel 130 adjacent to where the signal and noise detection channels 220A-B fluidly connect to the microchannel 130.

The signal and noise detection channels 210A-B may extend a distance D away from the microchannel 130 that is at least 2 times a width of the microchannel 130 adjacent to where the signal and noise detection channels 210A-B are fluidly connected to the microchannel 130, although other distances may be used. The signal and noise detection channels 210A-B may be balanced so that they receive about equal amounts of ambient electrical noise by configuring them to be structurally identical, such as configuring them to extend a same distance D away from the microchannel 130, to have a same volume extending away from the microchannel 130, and/or to have substantially the same cross sectional areas and length extending away from the microchannel 130. To maximize their electrical coupling to ambient electrical noise, the signal and noise detection channels 210A-B may be configured to extend in opposite directions that are substantially perpendicular to a flow direction of the adjacent microchannel 130.

Referring again to FIG. 1, in an alternative embodiment, a plurality of particle counting sensors 110 may be included downstream of the optical detection region 124 along the branched microchannel sorting pathways leading to one or more of the output ports 122A-D. Those downstream particle counting sensors 110 may be used in addition to or instead of the upstream particle counting sensor 110 shown in FIG. 1 to count total particles passing through the branched microchannels.

Figure 5:
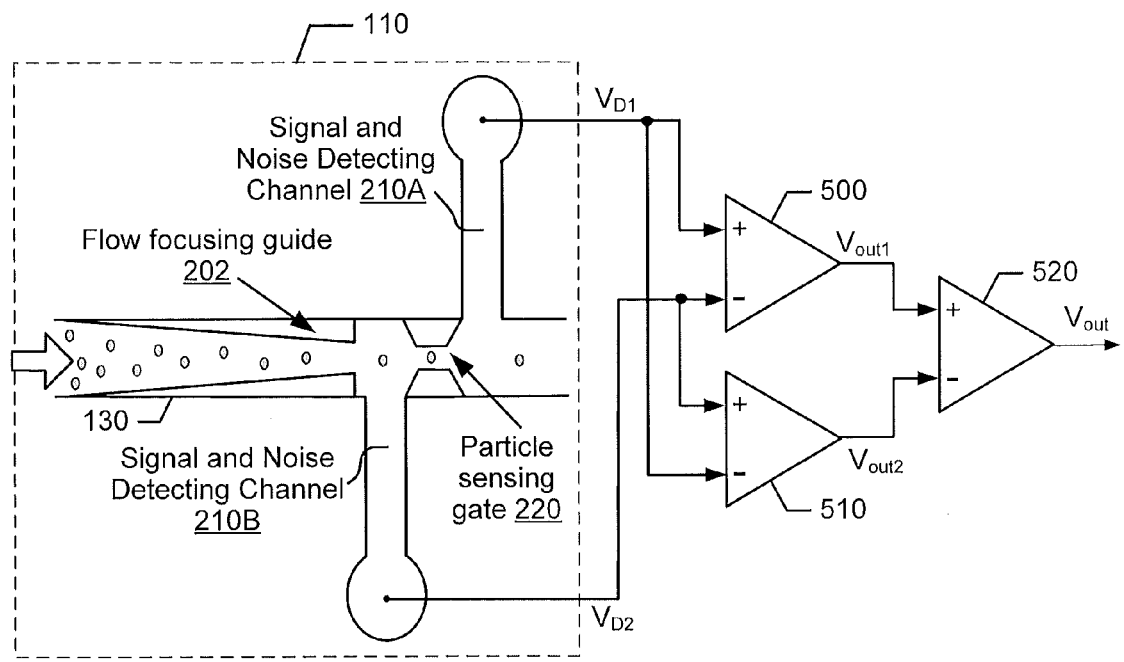
FIG. 5 is an enlarged view of the particle counting sensor of FIG. 2 and an associated dual-stage differential amplifier circuit which is configured according to some other embodiments of the present invention.

FIG. 5 is an enlarged view of the particle counting sensor 110 of FIG. 2 and an associated dual-stage differential amplifier circuit which is configured according to some other embodiments of the present invention. Referring to FIG. 5, the particle counting sensor 110 is identical to that shown in FIG. 2. However, in contrast to FIG. 2, a first stage of two differential amplifiers 500,510 are oppositely connected across the signal and noise detecting channels 210A-B and their respective output signals Vout1 and Vout2 are differentially amplified by a second stage differential amplifier 520 to generate the particle detection signal Vout. More particularly, a positive input terminal of the differential amplifier 500 is connected to an electrode in a fluid region of the detecting channel 210A and a negative input terminal of the differential amplifier 500 is connected to an electrode in a fluid region of the other detecting channel 210B. In contrast, a negative input terminal of the differential amplifier 510 is connected to the electrode in the detecting channel 210A and a positive input terminal of the differential amplifier 510 is connected to the electrode in the other detecting channel 210B. Particles flowing through the sensing gate 220 cause the first stage of differential amplifiers 500, 510 to generate output signals having a reduced common ambient noise component which is further canceled by the second stage differential amplifier 520, so that the particle detection signal Vout is substantially free of the received ambient electrical noise.

Figure 6:
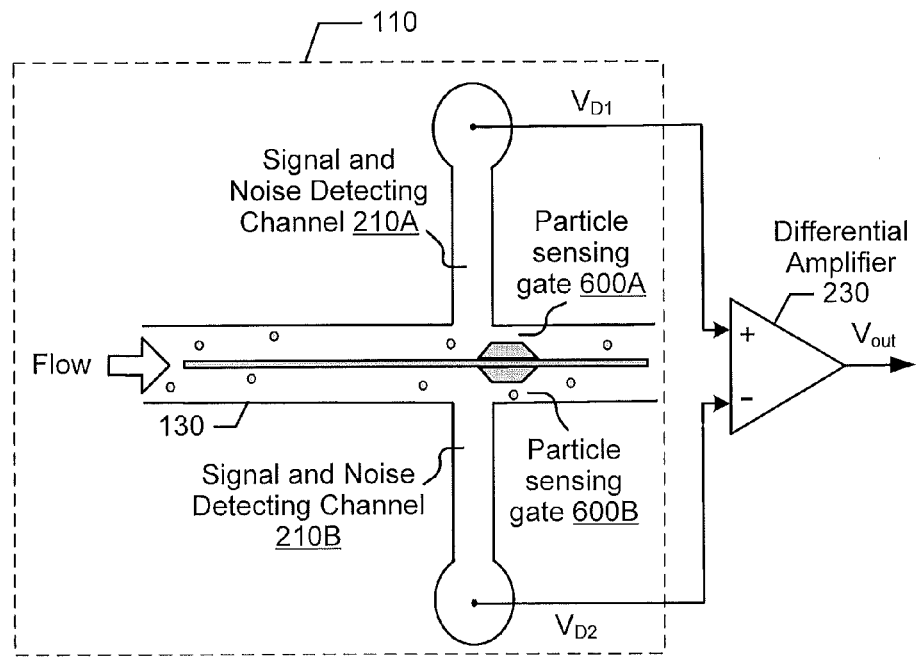
FIG. 6 is an enlarged view of the particle counting sensor of FIG. 1 and an associated differential amplifier circuit which are configured according to some other embodiments of the present invention.

FIG. 6 is an enlarged view of the particle counting sensor 110 and the associated differential amplifier circuit 230 of FIG. 1 which are configured according to some other embodiments of the present invention. In contrast to the particle sensing gate 220 shown in FIGS. 2 and 5, two particle sensing gates 600A-B are provided in the fluid path of the microchannel 130 of FIG. 6, and both signal and noise detecting channels 210A-B are aligned with each other and are fluidly connected to the microchannel 130 from a location that is adjacent to a same side of the particle sensing gates 600A-B.

Referring to FIG. 6, the sensing gates 600A-B are formed from a member that extends from a central region of the microchannel 130 toward opposite sidewalls of the microchannel 130 to provide two parallel reduced cross sectional areas through which fluid can flow. This configuration may increase the sensitivity of the particle detection circuit 110 by causing larger resistivity changes to occur between the central member and sidewalls of the microchannel 130 as individual particles flow therethrough. For some microfluidic flow cytometer applications, a distance across each region between the central member and the opposite sidewalls of the microchannel 130 may be in a range between about 1 μm to about 50 μm. Aligning the signal and noise detecting channels 210A-B as shown in FIG. 6 may decrease the width of the pulses generated by the differential amplifier circuit 230 as individual particles move through the particle sensing gates 600A-B, which may simplify the pulse counter circuitry which is configured to count the number of particles. A flow focusing guide, such as the guide 202 shown in FIG. 2, may be included upstream of the signal and noise detecting channels 210A-B to restrict the particles to traveling through the sensing gates 600A-B one at a time.

The Miniaturized Laser-Fiber Particle Optical Characterization and Sorting Apparatus.

Figure 7:
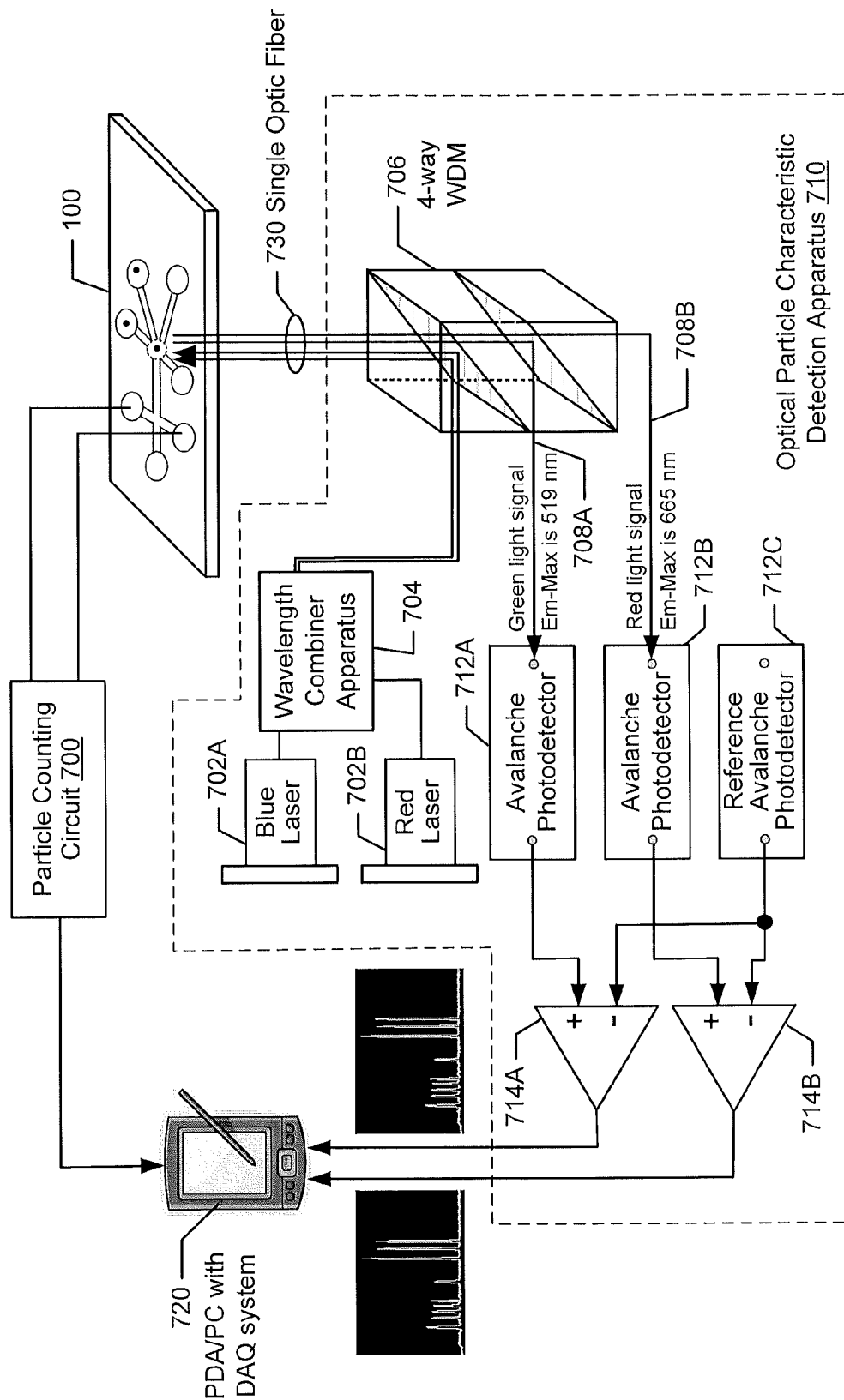
FIG. 7 is a block diagram of an exemplary apparatus that uses an electrokinetic microfluidic flow cytometer chip to count particles, to detect optical characteristics of particles, and to sort particles in accordance some embodiments of the present invention.
Figure 8:
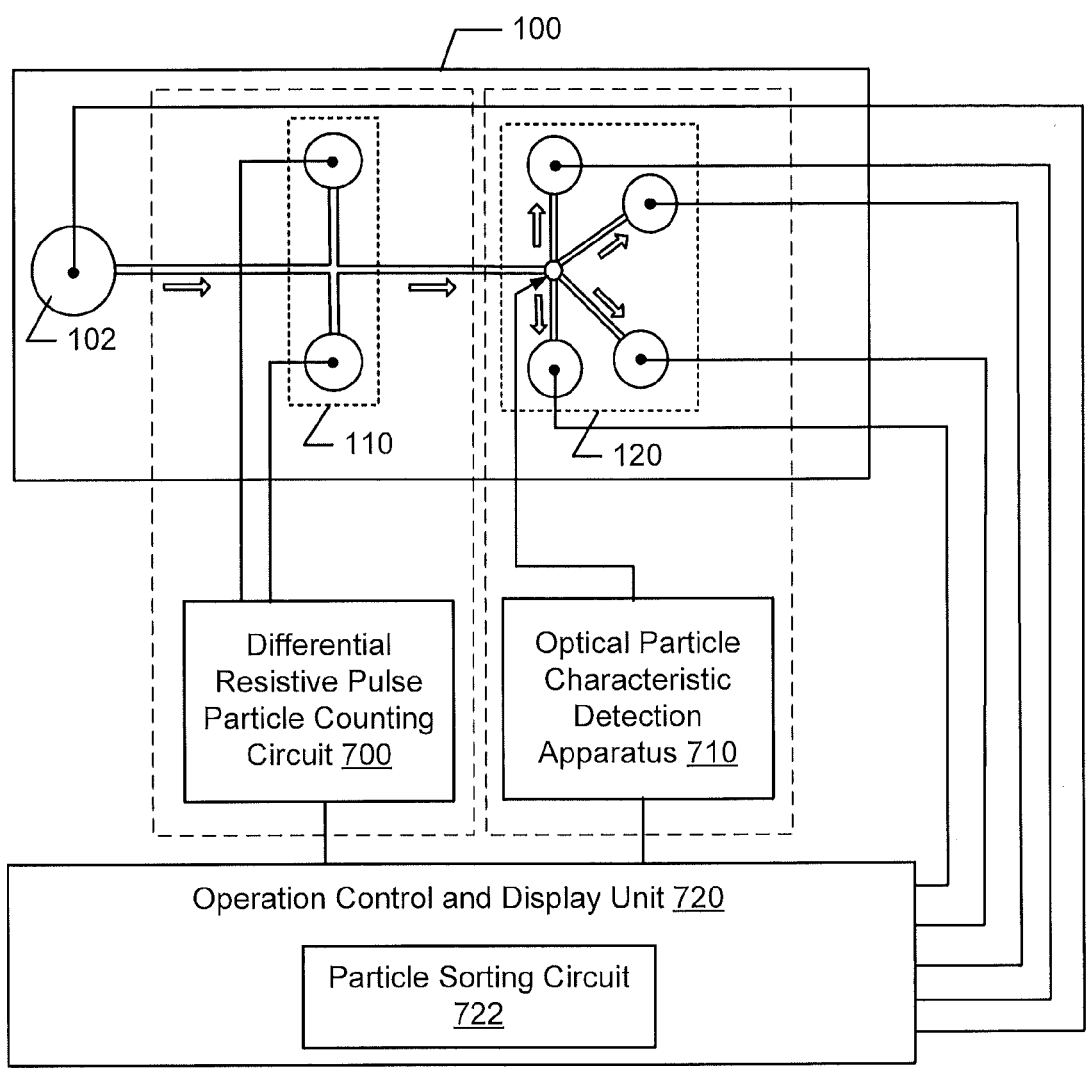
FIG. 8 is a further block diagram of the apparatus of FIG. 7 which is configured in accordance with some embodiments of the present invention.

FIGS. 7 and 8 are block diagrams of an exemplary laser-fiber particle optical characterization and sorting apparatus that counts particles, distinguishes between different particle types based on their optical characteristics, and sorts the particles according to their types in accordance with some embodiments of the present invention. Referring to FIGS. 7 and 8, the apparatus can include the cytometer chip 100 of FIG. 1, a particle counting circuit 700, a particle optical characterization apparatus 710, and an operation control and display unit 720.

The cytometer chip 100 may have the same or similar structure and operation to that described above for one or more of FIGS. 1-6. The particle counting circuit 700 can include the differential amplifier 230 of FIG. 2 to sense the differential voltage across the signal and noise detection channels while cancelling common ambient electrical noise to generate the particle detection signal. The particle counting circuit 700 may further count pulses in the particle detection signal or may provide the particle detection signal to the control unit 720 for counting.

The particle optical characterization apparatus 710 uses coherent laser light to illuminate and characterize particles passing through the optical detection region 124 of the chip 100. The control unit 720 uses the detected characteristics to classify the individual particles and may further control voltages between at least the particle detection region 124 and selected ones of the output ports 122A-D to sort the particles by type into the output ports.

The apparatus of FIG. 7 may be used to, for example, count the total number of cells within a blood sample, to identify and count specific types of blood cells that have been labeled with specific fluorescent dye, and to further sort the blood cells based on their identified types. Although the detection and sorting system is described in the context of using two wavelength lasers to detect biological cells, the invention is not limited thereto and may be used with any number of lasers, photodetectors, and wavelength light and, moreover, may be used to detect optical characteristics of any type of particle that is transported through the microfluidic channels.

To make the apparatus of FIG. 7 portable and/or to reduce its manufacturing complexity and cost (e.g., make the chip disposable), at least some embodiments of the invention do not use any embedded optical fibers or waveguides on the cytometer chip 100. Instead, a vertical detection configuration may be used as illustrated in FIG. 7. At least one optic fiber 730, which may be a single optic fiber, approaches the optical detection region 124 of the microchannel 130 from the bottom (or from the top) of the cytometer chip 100. A single multimode fiber (e.g., 100 μm core diameter) can be used to conduct a plurality of different coherent laser wavelengths to illuminate particles passing through the optical detection region 124. The optical fiber 730 can have a lens mounted at the tip to collect optical signals that are emitted by the illuminated particles. The particles can be labeled with defined fluorescent dye to emit a defined wavelength light when illuminated with a defined laser wavelength. A stage/fixture is designed to hold and align the fiber 730 with the optical detection region 124 of the cytometer chip 100.

Some further embodiments will now be described in the context of two-wavelength fluorescent detection using red and blue light, although a single wavelength may be used to detect particle characteristics or three or more different coherent wavelengths may be used to detect, classify, and/or sort three or more different types of particles. Two laser light sources 702A-B generate light (e.g., red light at 635 nm wavelength and blue light at 488 nm wavelength), which is combined into a single fiber by a laser combiner 704 and then provided to a 4-way WDM (wavelength-division multiplexer) 706 to be efficiently coupled to the multimode optic fiber 730 and shine on the optical detection region 124 of the cytometer chip 100. This embodiment is not limited to the use of red and blue lasers, instead the specific wavelength of the laser(s) that are used are selected based on what type of fluorescent dye is used to label the cells/particles. Although use of laser light sources may provide certain advantages by more accurately controlling emission of certain fluorescent dyed particles, the invention is not limited thereto and may be used with other light sources, such as with light emitting diodes.

The WDM 706 allows multiple optical carrier signals of different wavelengths to be carried by the single optical fiber 730 to the optical detection region 124. The WDM 706 has, in the present embodiment, two optic filters that are configured to pass the specific emission wavelengths for the specific dyes tagged on two different types of cells/particles. For example, a Cy5 filter can be used to detect AlexaFluor-647 emission, and a FITC filter can be used to detect AlexaFluor-488 emission.

The emission lights of different wavelengths will pass through the same optic fiber 730 and different filters in the WDM 706 to be directed into different output fibers 708A-B and be input into respective ones of two separate avalanche photodetectors 712A-B (or other light detection sensor device). The avalanche photodetectors are the semiconductor analog to a photomultiplier, providing very sensitive light detection but in much smaller size (about $3\times5\times1$ cm$^3$). Accordingly, the WDM 706 is configured to provide a first wavelength of light, when emitted by a particle, to a first avalanche photodetector 712A which responds by generating a first output signal, and to provide a different second wavelength of light, when emitted by a particle, to the second avalanche photodetector 712B which responds by generating a second output signal. The first and second output signals from the photodetectors 712A-B each contain a noise component due to, for example, temperature effects on and/or other properties of the analog circuitry of the photodetector sensors, sampling circuitry, and/or analog-digital circuitry. A reference photodetector 712C generates a reference noise signal that is not responsive to any light collected from the optical detection region of the microchannel. The reference photodetector 712C can be configured to have substantially the same operational characteristics as the photodetectors 712A-B, such as by being manufactured using the same processes, and, therefore, the reference noise signal characterizes the noise component in the output signals of the photodetectors 712A-B absent any light stimulus from an illuminated particle.

The reference noise signal can be subtracted from each of the output signals of the photodetectors 712A-B to at least substantially cancel the noise component therefrom and increase the signal-to-noise ratio of the compensated output signal. The compensated output signals can be provided to the control unit 720 to identify the type of particle that is present within the optical detection region 124. For example, a first differential amplifier 714A generates a first characteristic signal responsive to a difference between the first output signal from the photodetector 712A and the reference noise signal from the reference photodetector 712C so that the first characteristic signal is as at least substantially free of the noise component from the first output signal. Similarly, the second differential amplifier 714B generates a second characteristic signal responsive to a difference between the second output signal from the photodetector 712B and the reference noise signal from the reference photodetector 712C so that the second characteristic signal is as at least substantially free of the noise component from the second output signal. The first and second characteristic signals are fed to the control unit 720, such as via a data acquisition (DAQ) card/interface that may be inside of or external to the control unit 720.

The Operation Control and Display Unit.

The control unit 720 includes a central data processing unit, a data acquisition interface, a display device, and other electronic circuitry. Referring to FIG. 8, the control unit 720 is connected to electrodes that are positioned within a fluid carrying portion (spaced apart from sidewall material of the chip 100) of the input port 102 and the each of the output ports 122A-D. The control unit 720 and, more particularly, a particle sorting circuit 722 therein, regulates voltages that are applied between the input port 102 and selected ones of the output ports 122A-D to cause electroosmotic flow of the fluid from the input port 102 through the particle counting sensor 110 and the optical detection region 124 via the microchannel 130 into selected ones of the output ports 122A-D to sort the particles responsive to their detected optical characteristics.

For example, the particle sorting circuit 722 may supply 50V, another voltage, or a time varying range of voltages, between the input port 102 and a first output port 122A to move a first detected type of particle from the optical detection region 124 to the first output port 122A. When a second type of particle is detected by the apparatus 710, the particle sorting circuit 722 can supply the voltage between the input port 102 and a second output port 122B to move the particle to the second output port 122B. Similarly, the particle sorting circuit 722 can selectively supply the voltage between the input port 102 and a selected one of the third and fourth output ports 122C-D to move a third type of particle and a fourth type of particle to the third output port 122C or the fourth output port 122D, respectively.

The control unit 720 may be any type of data processing circuit, such as a Personal Data Assistant, a cellular smart phone, a palmtop computer, a laptop computer, a desktop computer, etc.

As explained above, the apparatus of FIGS. 7 and 8 may be used to count the number of CD4+ cells relative to the total number of cells within a blood sample. Once a fluorescent signal is detected, for example a green light from a CD4+ cell is detected, this means that a CD4 cell is passing through the optical detection region 124. This CD4 cell will be counted and recorded in the control unit 720. At about the same time, a pulse electric field is generated by the particle sorting circuit 722 to produce a pulse flow to transport this CD4 cell to a selected one of the output ports 122A-D to be sorted or collected there. The control unit 720 may display on a display device an indication of the number of counted CD4 cells, as determined by the particle characteristic detection apparatus 710, and an indication of the total number of counted cells, as determined by the particle counting circuit 700, and/or it may display the percentage of CD4 cells relative to other cells in the sample. This information can be used to detect, for example, HIV disease and/or characterize its progress stage.

FIG. 9 is a graph that illustrates a particle characterization voltage signal that was output during operation of an exemplary particle optical characterization apparatus similar to that illustrated in FIGS. 1 and 7 (e.g., the signal output by one of the differential amplifiers in FIG. 7). The voltage signal identifies by pulsed changes when individual fluorescent dyed CD4 cells within a blood sample have entered the optical detection region and emitted a particular wavelength light responsive to illumination by the coherent laser light. The voltage signal can therefore be used to count the total number of CD4 cells in the sample.

FIG. 10 is a graph illustrating a particle counting current signal that was output during operation of the particle counting sensor of the exemplary apparatus of FIGS. 1 and 7 as a sequence of blood particles, including some CD4 cells, move one by one through the particle sensing gate of the particle counting sensor. The current signal identifies by pulsed changes when individual blood particles, including some CD4 cells, moves one by one through the particle counting sensor. The current signal can therefore be used to count the total number of cells in the sample.

Figure 11:
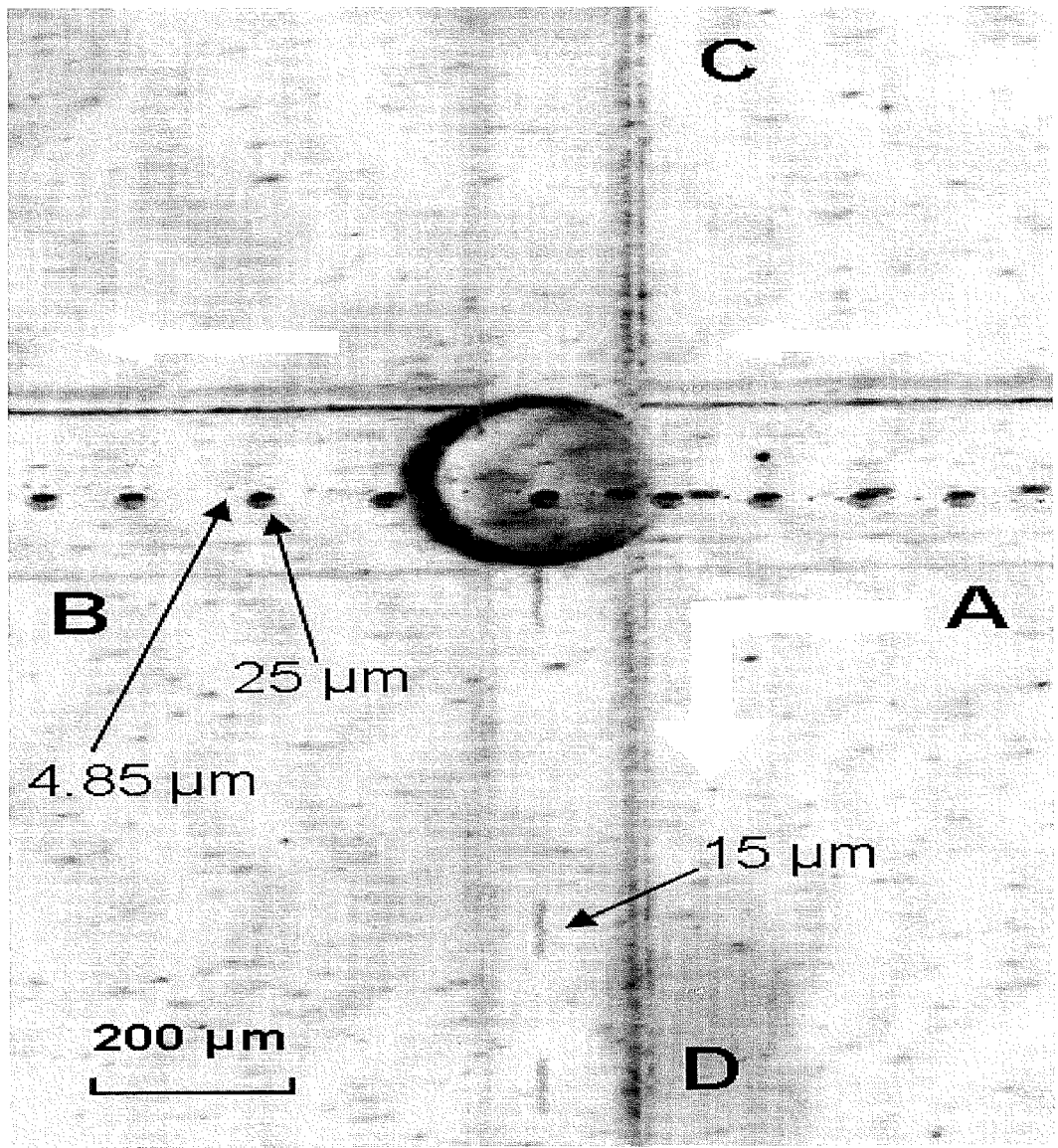
FIG. 11 is a time-lapsed microphotograph of an exemplary optical characterization and particle sorting region of a microchannel that is configured in accordance with some embodiments of the present invention.

FIG. 11 is a time-lapsed microphotograph of an exemplary optical detection and particle sorting region of a microchannel, such as region 124 in FIG. 1, in accordance with some embodiments of the present invention. This picture shows the trajectories of a 15 μm fluorescent particle and 4.85 and 25 μm non-fluorescent particles as they are sorted from the input microchannel A between output microchannels B,C,D by controlling electrical voltages between the detection and particle sorting region and the associated output ports. The picture was obtained by superposing a series of consecutive images taken of the moving particles. The 15 μm particle shows longer streaks in the picture because of its increased velocity in the dispensing microchannel branch D. Under the same exposure time, faster motion causes longer streaks. The darkened circuit at the junction of the microchannel branches A,B,C,D is the list of the optic fiber (e.g., fiber 730 in FIG. 7) which carries a plurality of different coherent laser light wavelengths to detect optical characteristics of the particles for use in sorting the particles.

Operation of the Handheld Flow Cytometer Lab-on-a-Chip Device.

Figure 12:
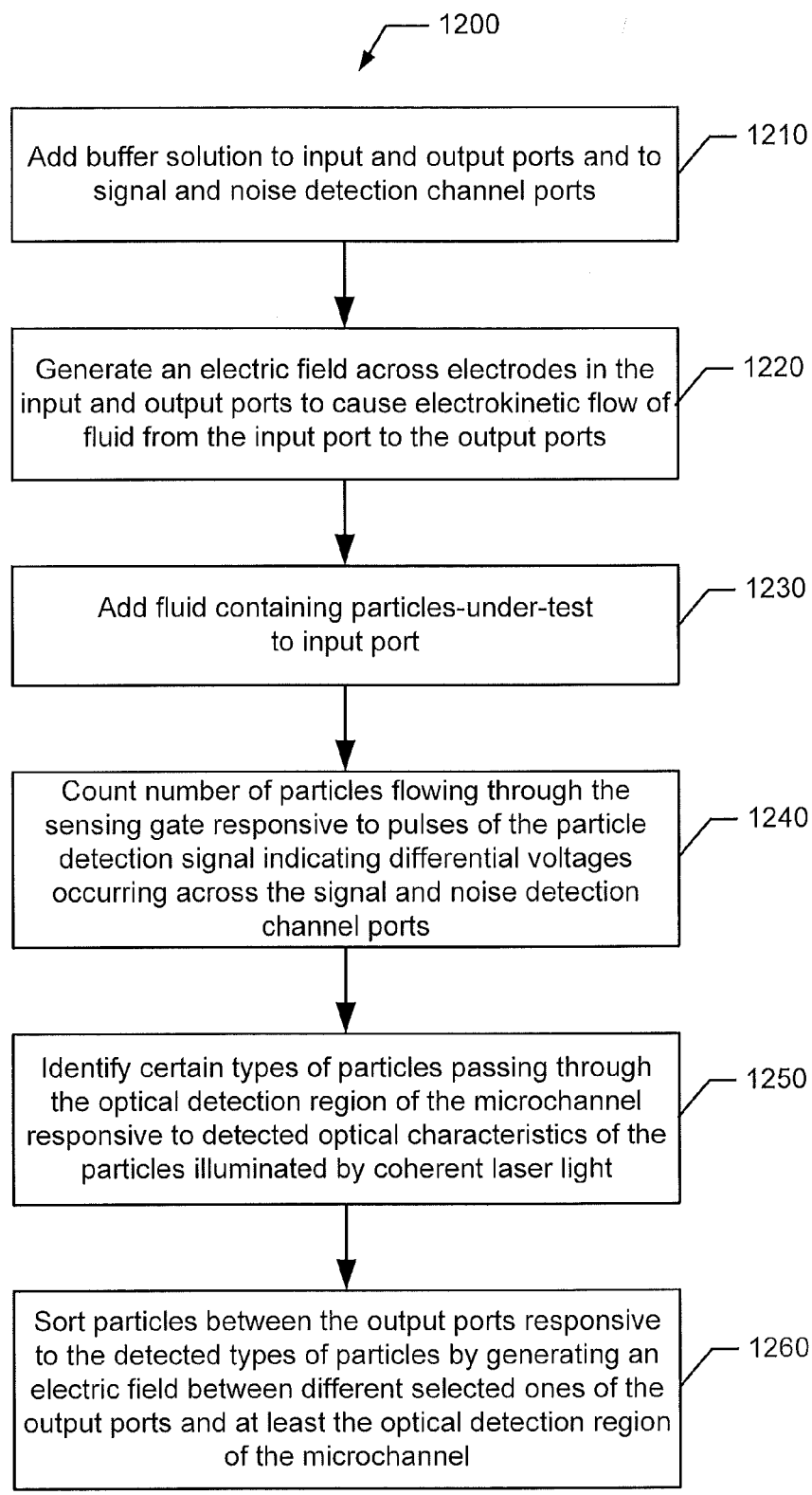
FIG. 12 is a flowchart that illustrates various operations that can be carried out using the electrokinetic microfluidic flow cytometer chip of FIG. 1 to count, characterize and sort particles within a fluid sample.

Exemplary operations that may be carried out to perform analysis of a fluid sample using the apparatus of FIGS. 1-11 are shown in the flowchart of FIG. 12. Referring to FIG. 12, a microfluidic flow cytometer chip is placed in the chip-holding stage which ensures the precise alignment between the optical fiber and the fluorescent detection spot, and between the electrodes and ports. A pipette may be used to add buffer solution to the input and output ports, and may be further added to the signal and noise detection channel ports (block 1210). A sample fluid that is to be tested is added to the input port (block 1220). An electric field is generated across electrodes and the input and output ports to cause electrokinetic flow of fluid from the input port to the output ports and, thereby, fill the microchannel(s) (block 1230). The number of particles flowing through the sensing gate is counted responsive to pulses of the particle detection signal, which indicate differential voltages occurring across the signal and noise detection channel ports (block 1240). The types of particles passing through the optical detection region of the microchannel are identified responsive to their optical characteristics when illuminated with one or more coherent laser light wavelengths (block 1250). The particles are then sorted between the output ports responsive to their detected types, by generating electric fields between different selected ones of output ports and at least the optical detection region of the microchannel (block 1260). Various of the operations of Blocks 1220 and 1240-1260 can be performed by a microprocessor in the control unit 720 of FIG. 8 executing software residing in a computer readable memory circuit. The control unit 720 can include a display, such as a liquid crystal display on a PDA, to display results of the analysis in real time as the sample fluid is being analyzed.

Using the microfluidic chip, the amount of (blood) sample and reagents may be dramatically reduced from hundreds of micro liters to one-to-tens of micro liters. Such volume reductions can significantly reduce the cost of the associated reagents which are used during the analysis process. Embodiments of the device may be configured to be handheld, entirely self-contained, fully automatic and run on battery power. The capital cost of such flow cytometers may be significantly reduced from $75,000-$125,000 to under a few thousand dollars.

In the drawings and specification, there have been disclosed embodiments of the invention and, although specific terms are employed, they are used in a generic and descriptive sense only and not for purposes of limitation, the scope of the invention being set forth in the following claims.

What is claimed:

1. An electrokinetic microfluidic flow cytometer apparatus comprising:
a substrate having defined therein an input port, an output port, and a microchannel that fluidly connects the input port and the output port to allow fluid to flow therebetween;
a pair of signal and noise detection channels that are defined in the substrate and fluidly connected to the microchannel from locations adjacent to each other and which extend in opposite directions away from the microchannel to receive ambient electrical noise; and
a particle detection circuit that is electrically connected to the signal and noise detection channels and generates a particle detection signal in response to a differential voltage across the signal and noise detection channels, which tracks changes in resistivity across an adjacent portion of the microchannel as particles within the fluid move responsive to an electric field along that portion of the microchannel, while at least substantially canceling a common component of the ambient electrical noise received by the signal and noise detection channels; and
a sensing gate that reduces the cross sectional area of the microchannel through which fluid carrying particles can flow, wherein the signal and noise detection channels are fluidly connected to the microchannel adjacent to the sensing gate, and wherein the particle detection circuit generates the particle detection signal responsive to resistivity changes that occur across the sensing gate as particles flow through the sensing gate under electrokinetic force,
wherein the sensing gate reduces the width of the microchannel through which fluid can flow to less than about ten times a width of individual particles that are to be sensed as they flow within fluid through the sensing gate.

2. The electrokinetic microfluidic flow cytometer apparatus of claim 1, further comprising:
a particle counting circuit that counts a number of particles moving past the signal and noise detection channels in response to pulses in the particle detection signal.

3. The electrokinetic microfluidic flow cytometer apparatus of claim 1, wherein:
the sensing gate has a length between about 5 μm to about 100 μm along which it reduces the width of the microchannel.

4. The electrokinetic microfluidic flow cytometer apparatus of claim 1, wherein:
the signal and noise detection channels are fluidly connected to portions of the microchannel that are spaced apart and immediately adjacent to opposite sides of the sensing gate.

5. The electrokinetic microfluidic flow cytometer apparatus of claim 1, wherein:
the signal and noise detection channels are fluidly connected to opposite facing sidewalls of a portion of the microchannel that are immediately adjacent to a same side of the sensing gate.

6. The electrokinetic microfluidic flow cytometer apparatus of claim 1, wherein:
the sensing gate comprises a pair of members that extend toward each other from opposite facing sidewalls of a portion of the microchannel to reduce the cross sectional area of the microchannel through which the fluid flows and increase sensitivity of the particle detection circuit to resistivity changes that occur between the members as individual particles flow between the members within the microchannel.

7. The electrokinetic microfluidic flow cytometer apparatus of claim 1, wherein:
the sensing gate comprises a member that extends from a central region of the microchannel toward opposite sidewalls of the microchannel to reduce the cross sectional area of the microchannel through which fluid can flow and increase sensitivity of the particle detection circuit to resistivity changes that occur between the member and sidewalls of the microchannel as individual particles flow therethrough.

8. The electrokinetic microfluidic flow cytometer apparatus of claim 7, wherein:
a distance across each region between the member and the opposite sidewalls of the microchannel is in a range between about 1 μm to about 50 μm.

9. The electrokinetic microfluidic flow cytometer apparatus of claim 1, further comprising:
at least two electrodes, one of which is positioned within the input port and the other of which is positioned within the output port;
a control circuit that controls application of an electric voltage across the electrodes to create an electric field along the microchannel and electrokinetic force which transports fluid from the input port to the output port; and
a sensing gate that reduces the cross sectional area of the microchannel through which fluid carrying particles can flow, wherein the signal and noise detection channels are fluidly connected to the microchannel adjacent to the sensing gate, and wherein the particle detection circuit generates the particle detection signal responsive to resistivity changes that occur across the sensing gate as particles flow through the sensing gate in the presence of the electric field along the microchannel.

10. The electrokinetic microfluidic flow cytometer apparatus of claim 1, further comprising a sensing gate that reduces the cross sectional area of the microchannel through which fluid carrying particles can flow, wherein:
the signal and noise detection channels are fluidly connected to the microchannel adjacent to the sensing gate and extend a same distance away from the sensing gate and the microchannel to be configured to receive about equal amounts of ambient electrical noise, and
the particle detection circuit is configured to substantially cancel the ambient electrical noise received from the signal and noise detection channels while generating the particle detection signal responsive to resistivity changes that occur across the sensing gate as particles flow through the sensing gate.

11. The electrokinetic microfluidic flow cytometer apparatus of claim 10, wherein:
the signal and noise detection channels extend in opposite directions that are substantially perpendicular to a flow direction of the adjacent microchannel to increase the electrical coupling of the signal and noise detection channels to ambient electrical noise.

12. The electrokinetic microfluidic flow cytometer apparatus of claim 1, wherein:
the signal and noise detection channels each have a same volume extending away from the microchannel to be configured to receive about equal amounts of ambient electrical noise; and
the particle detection circuit is configured to substantially cancel the ambient electrical noise received from the signal and noise detection channels when generating the particle detection signal.

13. The electrokinetic microfluidic flow cytometer apparatus of claim 12, wherein:
the signal and noise detection channels have substantially the same cross sectional areas and length to be configured to receive about equal amounts of ambient electrical noise.

14. The electrokinetic microfluidic flow cytometer apparatus of claim 1, further comprising:
a first pair of electrodes, wherein each electrode is positioned in a space within a different one of the signal and noise detection channels that is fluidly connected to the microchannel, and wherein the particle detection circuit is electrically connected to the electrodes and generates the particle detection signal responsive to differential voltage across the first pair of electrodes.

15. The electrokinetic microfluidic flow cytometer apparatus of claim 14, wherein:
the particle detection circuit comprises a differential amplifier having a pair of input terminals, one of the input terminals is connected to one of the electrodes within one of the signal and noise detection channels and the other one of the input terminals is connected to the other one of the electrodes within the other one of the signal and noise detection channels.

16. The electrokinetic microfluidic flow cytometer apparatus of claim 1, wherein the output port comprises a plurality of particle sorting output ports that are defined in the substrate and are fluidly connected to an optical detection region of the microchannel on an opposite side of the signal and noise detection channels from the input port, and further comprising:
a particle optical characterization apparatus that detects an optical characteristic of at least one particle in a fluid within the optical detection region of the microchannel; and
a particle sorting circuit that separately controls voltages that are applied between each of the particle sorting output ports and at least the optical detection region of the microchannel in response to the detected optical characteristic of the at least one particle to transport the at least one particle by electrokinetic flow of the fluid from the optical detection region to a selected one of the output ports.

17. An electrokinetic microfluidic flow cytometer apparatus comprising:
a substrate having defined therein an input port, an output port, and a microchannel that fluidly connects the input port and the output port to allow fluid to flow therebetween;
a pair of signal and noise detection channels that are defined in the substrate and fluidly connected to the microchannel from locations adjacent to each other and which extend in opposite directions away from the microchannel to receive ambient electrical noise; and
a particle detection circuit that is electrically connected to the signal and noise detection channels and generates a particle detection signal in response to a differential voltage across the signal and noise detection channels, which tracks changes in resistivity across an adjacent portion of the microchannel as particles within the fluid move responsive to an electric field along that portion of the microchannel, while at least substantially canceling a common component of the ambient electrical noise received by the signal and noise detection channels; and
a sensing gate that reduces the cross sectional area of the microchannel through which fluid carrying particles can flow, wherein the signal and noise detection channels are fluidly connected to the microchannel adjacent to the sensing gate, and wherein the particle detection circuit generates the particle detection signal responsive to resistivity changes that occur across the sensing gate as particles flow through the sensing gate under electrokinetic force, wherein the sensing gate comprises a pair of members that extend toward each other from opposite facing sidewalls of a portion of the microchannel to reduce the cross sectional area of the microchannel through which the fluid flows and increase sensitivity of the particle detection circuit to resistivity changes that occur between the members as individual particles flow between the members within the microchannel, and a distance across the fluid flow region between the members is in a range between about 1 µm to about 50 µm.

18. An electrokinetic microfluidic flow cytometer apparatus comprising:

a substrate having defined therein an input port, an output port, and a microchannel that fluidly connects the input port and the output port to allow fluid to flow therebetween;

a pair of signal and noise detection channels that are defined in the substrate and fluidly connected to the microchannel from locations adjacent to each other and which extend in opposite directions away from the microchannel to receive ambient electrical noise; and a particle detection circuit that is electrically connected to the signal and noise detection channels and generates a particle detection signal in response to a differential voltage across the signal and noise detection channels, which tracks changes in resistivity across an adjacent portion of the microchannel as particles within the fluid move responsive to an electric field along that portion of the microchannel, while at least substantially canceling a common component of the ambient electrical noise received by the signal and noise detection channels;

a sensing gate that reduces the cross sectional area of the microchannel through which fluid carrying particles can flow, wherein the signal and noise detection channels are fluidly connected to the microchannel adjacent to the sensing gate, and wherein the particle detection circuit generates the particle detection signal responsive to resistivity changes that occur across the sensing gate as particles flow through the sensing gate under electrokinetic force; and a flow focusing guide having a converging cross sectional fluid flow area along the flow direction with a cross sectional fluid flow output area that restricts particles flowing therethrough to exiting one at a time, wherein the flow focusing guide is positioned upstream of the sensing gate along the microchannel.

19. An electrokinetic microfluidic flow cytometer apparatus comprising:

a substrate having defined therein an input port, an output port, and a microchannel that fluidly connects the input port and the output port to allow fluid to flow therebetween;

a pair of signal and noise detection channels that are defined in the substrate and fluidly connected to the microchannel from locations adjacent to each other and which extend in opposite directions away from the microchannel to receive ambient electrical noise; and a particle detection circuit that is electrically connected to the signal and noise detection channels and generates a particle detection signal in response to a differential voltage across the signal and noise detection channels, which tracks changes in resistivity across an adjacent portion of the microchannel as particles within the fluid move responsive to an electric field along that portion of the microchannel, while at least substantially canceling a common component of the ambient electrical noise received by the signal and noise detection channels, wherein a cross-sectional area of each signal and noise detection channel is less than a cross-sectional area of the microchannel adjacent to where the signal and noise detection channels fluidly connect to the microchannel.

20. The electrokinetic microfluidic flow cytometer apparatus of claim 19, wherein:

a width of each signal and noise detection channel is less than half a width of the microchannel adjacent to where the signal and noise detection channels fluidly connect to the microchannel.

21. The electrokinetic microfluidic flow cytometer apparatus of claim 19, wherein:

the signal and noise detection channels extend a distance away from the microchannel that is at least 2 times a width of the microchannel adjacent to where the signal and noise detection channels are fluidly connected to the microchannel.

22. An electrokinetic microfluidic flow cytometer apparatus comprising:

a substrate having defined therein an input port, a plurality of particle sorting output ports, and a microchannel that fluidly connects the input port and the plurality of particle sorting output ports to allow fluid to flow therebetween responsive to an electric field along the microchannel;

at least one optical fiber that is positioned to guide at least one wavelength of light from at least one light source to illuminate an optical detection region of the microchannel and to collect light that is emitted from at least one particle present in fluid within the optical detection region;

a first primary photodetector that is connected to the at least one optical fiber to receive at least first wavelength light therefrom and configured to generate a first output signal responsive thereto, the first output signal containing a noise component;

a reference photodetector that generates a reference noise signal that is not responsive to any light collected from the optical detection region of the microchannel and is characteristic of the noise component in the first output signal; and a first comparator circuit that generates a first characterization signal responsive to a difference between the first output signal and the reference noise signal so that the first characterization signal is at least substantially free of the noise component from the first output signal.

23. The electrokinetic microfluidic flow cytometer apparatus of claim 22, wherein:

the reference photodetector is configured to have substantially the same operational characteristics as the first primary photodetector.

24. The electrokinetic microfluidic flow cytometer apparatus of claim 23, wherein:

the first comparator circuit comprise a differential amplifier having a pair of input terminals;

one of the input terminals is connected to receive the first output signal from the first primary photodetector and the other input terminal is connected to receive the reference noise signal from the reference photodetector; and the differential amplifier is configured to generate a first particle characterization signal responsive to a voltage difference between the input terminals that indicates a detected optical characteristic of a particle within the optical detection region responsive to illumination by the at least one wavelength of light.

25. The electrokinetic microfluidic flow cytometer apparatus of claim 22, further comprising a control circuit that is configured to classify the particle as being a defined particle type in response to the first particle characterization signal.

26. The electrokinetic microfluidic flow cytometer apparatus of claim 22:
wherein the at least one optical fiber is positioned to guide at least two wavelengths of coherent laser light from at least two laser light sources to illuminate the optical detection region of the microchannel and to collect light that is emitted from the least one particle present in fluid within the optical detection region;
further comprising a filter apparatus that is configured to receive the light collected by the at least one optical fiber and to split the collected light to pass a plurality of different defined wavelengths, when present, through different corresponding ones of a plurality of filter output fibers;
wherein the first primary photodetector is connected to receive a first wavelength light through one of the filter output fibers and to generate the first output signal responsive thereto;
further comprising at least a second primary photodetector that is connected to receive a second wavelength light through another one of the filter output fibers and to generate a second output signal responsive thereto, the second output signal containing a noise component,
wherein the reference photodetector is configured to have substantially the same operational characteristics as the first and second primary photodetectors and the reference noise signal is further characteristic of the noise component in the second output signal; and
further comprising at least a second comparator circuit that generates a second particle characterization signal responsive to a difference between the second output signal and the reference noise signal so that the second particle characterization signal is at least substantially free of the noise component from the second output signal.

27. The electrokinetic microfluidic flow cytometer apparatus of claim 26, further comprising a control circuit that is configured to classify the particle as being one of a plurality of different defined particle types in response to the first and second particle characterization signals.

28. The electrokinetic microfluidic flow cytometer apparatus of claim 26, wherein:
the filter apparatus is configured to split the collected light to pass a green wavelength component of the collected light through a first filter output fiber to the first primary photodetector and to pass a red wavelength light component of the collected light through a second filter output fiber to the second primary photodetector;
the first particle characterization signal indicates when the at least one particle present in the fluid within the optical detection region emits green light responsive to the illumination; and
the second particle characterization signal indicates when the at least one particle present in the fluid within the optical detection region emits red light responsive to the illumination.

29. The electrokinetic microfluidic flow cytometer apparatus of claim 26, further comprising:
a particle sorting circuit that separately controls voltages between each of the particle sorting output ports and at least the optical detection region of the microchannel in response to the first and second characterization signals to transport the at least one particle by electrokinetic flow of the fluid from the optical detection region to one of the output ports that is selected responsive to the first and second particle characterization signals.

30. The electrokinetic microfluidic flow cytometer apparatus of claim 26, wherein:
the at least one particle comprises a plurality of different types of blood cells, at least two of the types of blood cells are labeled with different fluorescent dyes that emit different defined wavelengths of light responsive to illumination by the coherent laser light;
the first primary photodetector generates the first output signal responsive to first wavelength light being received from the filter apparatus;
the first differential amplifier regulates the first particle characterization signal to indicate that a first type of blood cell is present in the optical detection region of the microchannel in response to the first output signal differing from the reference noise signal by at least a threshold amount; and
the second primary photodetector generates the second output signal responsive to second wavelength light being received from the filter apparatus; and
the second differential amplifier regulates the second particle characterization signal to indicate that a second type of blood cell is present in the optical detection region of the microchannel in response to the second output signal differing from the reference noise signal by at least a threshold amount.

31. The electrokinetic microfluidic flow cytometer apparatus of claim 30, further comprising:
a particle sorting circuit that separately controls voltages between each of the particle sorting output ports and at least the optical detection region of the microchannel in response to the first and second particle characterization signals to sort the detected types of blood cells by controlling electrokinetic flow of the fluid from the optical detection region to different ones of the output ports.

32. The electrokinetic microfluidic flow cytometer apparatus of claim 26, wherein the filter apparatus comprises a wavelength division multiplexing (WDM) filter apparatus that is configured to direct a combined plurality of wavelengths of coherent laser light through a single optical fiber that is positioned to illuminate the optical detection region of the microchannel with the combined wavelength light and to collect light that is reflected therefrom, and is configured to receive the light collected by the single optical fiber and to split the collected light so that a plurality of different defined wavelengths, when present, pass through different corresponding ones of the plurality of filter output fibers.

33. The electrokinetic microfluidic flow cytometer apparatus of claim 32, wherein:
the single optical fiber is positioned to illuminate the optical detection region of the microchannel from a same side of the substrate from which the input port and the plurality of particle sorting output ports are exposed.

34. The electrokinetic microfluidic flow cytometer apparatus of claim 32, further comprising:
a wavelength combiner apparatus that is configured to receive light from a plurality of different laser sources and to combine the received light to generate the combined plurality of wavelengths of coherent laser light that is provided to the WDM filter apparatus to be directed through the single optical fiber to illuminate the optical detection region of the microchannel.

* * * * *